(12) United States Patent
Iizuka

(10) Patent No.: US 12,279,821 B2
(45) Date of Patent: Apr. 22, 2025

(54) REFRACTIVE PROPERTY MEASUREMENT DEVICE, MEASUREMENT TOOL, AND REFRACTIVE PROPERTY MEASUREMENT METHOD

(71) Applicant: HOYA LENS THAILAND LTD., Pathumthani (TH)

(72) Inventor: Takashi Iizuka, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 817 days.

(21) Appl. No.: 17/312,835

(22) PCT Filed: Dec. 11, 2019

(86) PCT No.: PCT/JP2019/048380
§ 371 (c)(1),
(2) Date: Jun. 10, 2021

(87) PCT Pub. No.: WO2020/137533
PCT Pub. Date: Jul. 2, 2020

(65) Prior Publication Data
US 2022/0054005 A1 Feb. 24, 2022

(30) Foreign Application Priority Data

Dec. 28, 2018 (JP) .............................. 2018-247322

(51) Int. Cl.
*A61B 3/103* (2006.01)
*A61B 3/00* (2006.01)

(52) U.S. Cl.
CPC ............ *A61B 3/103* (2013.01); *A61B 3/0008* (2013.01); *A61B 3/0025* (2013.01)

(58) Field of Classification Search
CPC ..... A61B 3/103; A61B 3/0008; A61B 3/0025; A61B 3/00; A61B 3/0075; A61B 3/113;
(Continued)

(56) References Cited

U.S. PATENT DOCUMENTS 2,933,977 A * 4/1960 Landis ................... A61B 3/036
351/232
3,841,760 A   10/1974 Guyton
(Continued)

FOREIGN PATENT DOCUMENTS

CN  106249412 A  12/2016
CN  111616674 A   9/2020
(Continued)

OTHER PUBLICATIONS

Dec. 13, 2023 Office Action issued in European Patent Application No. 19902783.0.
(Continued)

*Primary Examiner* — Jie Lei
(74) *Attorney, Agent, or Firm* — Oliff PLC

(57) ABSTRACT

A refractive property measurement apparatus to measure refractive properties of an eye includes: a disk provided with a first pinhole and a second pinhole that transmit light rays while narrowing them; a light emitting unit that emits a first light ray and a second light ray from different positions on a surface of the disk, so that light rays passed through the first pinhole and the second pinhole enter the eye; and a processing unit determines refractive properties of the eye from information of positions on a retina of the eye where the first light ray having passed through the first pinhole and the second light ray having passed through the second pinhole reach. The first pinhole includes a first optical element that transmits the first light ray, and the second pinhole includes a second optical element that has transmission characteristics of transmitting the second light ray.

10 Claims, 6 Drawing Sheets

(58) Field of Classification Search
CPC ........... A61B 3/117; A61B 3/02; A61B 3/028;
A61B 3/032; A61B 3/04; A61B 3/15;
A61B 3/152; A61B 3/156; A61B 3/14;
A61B 3/145; A61B 3/12; A61B 5/14546
USPC ....... 351/214, 210, 211, 216, 200, 205, 206,
351/208, 203, 221, 232, 237, 236, 243,
351/246
See application file for complete search history.

(56) References Cited

U.S. PATENT DOCUMENTS

| | | | |
|---|---|---|---|
| 4,134,644 A * | 1/1979 | Marks | G02B 27/1006 |
| | | | 348/E13.058 |
| 4,778,268 A | 10/1988 | Randle | |
| 4,943,151 A | 7/1990 | Cushman | |
| 4,973,151 A | 11/1990 | Bryant | |
| 5,988,814 A * | 11/1999 | Rohlfing | A61B 3/028 |
| | | | 351/212 |
| 6,687,003 B1 * | 2/2004 | Sorensen | H04N 13/15 |
| | | | 348/E13.058 |
| 7,370,964 B2 * | 5/2008 | Wakil | A61B 3/0091 |
| | | | 351/203 |
| 8,783,871 B2 | 7/2014 | Pamplona et al. | |
| 9,271,646 B2 * | 3/2016 | Neal | A61B 3/0033 |
| 10,278,573 B2 * | 5/2019 | Boutinon | A61B 3/04 |
| 10,980,412 B2 * | 4/2021 | Takii | A61B 3/103 |
| 2002/0140903 A1 | 10/2002 | Schachar | |
| 2004/0032567 A1 | 2/2004 | Fukuma et al. | |
| 2004/0032568 A1 | 2/2004 | Fukuma et al. | |
| 2016/0363770 A1 | 12/2016 | Kim et al. | |
| 2018/0242837 A1 | 8/2018 | Nauche et al. | |
| 2020/0221943 A1 | 7/2020 | Kobayashi et al. | |
| 2021/0386285 A1 | 12/2021 | Walsh et al. | |

FOREIGN PATENT DOCUMENTS

| | | |
|---|---|---|
| EP | 1138253 A2 | 10/2001 |
| EP | 1433415 A2 | 6/2004 |
| EP | 1 752 084 A2 | 2/2007 |
| EP | 3106911 A1 | 12/2016 |
| EP | 3903663 A1 | 11/2021 |
| GB | 148754 A | 1/1921 |
| JP | 2001-340296 A | 12/2001 |
| JP | 6308277 B2 | 4/2018 |
| JP | 2020-103743 A | 7/2020 |
| KR | 10-2016-0147636 A | 12/2016 |
| WO | 2002/078530 A1 | 10/2002 |
| WO | 2015/118634 A1 | 8/2015 |
| WO | 2016/204433 A1 | 12/2016 |
| WO | 2017/037386 A1 | 3/2017 |

OTHER PUBLICATIONS

Mar. 3, 2020 International Search Report issued in International Patent Application No. PCT/JP2019/048380.
Thibos N. Larry, "Principles of Hartmann-Shack Aberrometry", Journal of Refractive Surgery, Oct. 31, 2000, vol. 16, pp. S563-S565.
1 Nov. 1, 2023 Office Action issued in Chinese Patent Application No. 201980086436.8.
Sep. 6, 2022 Office Action issued in Japanese Patent Application No. 2018-247322.
Feb. 8, 2022 Extended European Search Report issued in European Patent Application No. 21199310.0.
Jun. 21, 2021 U.S. Appl. No. 17/312,835 filed in the name of inventor Takashi Iizuka.
Jan. 27, 2022 Extended European Search Report issued in European Patent Application No. 19902783.0.
Victor F. Pamplona et al: "NETRA: Interactive Display for Estimating Refractive Errors and Focal Range", ACM Transactions on Graphics, ACM, NY, US, vol. 29, No. 4, Jul. 26, 2010.
Nov. 7, 2024 Notice Of Allowance Issued in U.S. Appl. No. 17/485,873.

* cited by examiner

REFRACTIVE PROPERTY MEASUREMENT DEVICE, MEASUREMENT TOOL, AND REFRACTIVE PROPERTY MEASUREMENT METHOD

FIELD

The present invention relates to a refractive property measurement apparatus for measuring refractive properties of an eye, a refractive property measurement method, and a measurement tool for use in measuring refractive properties of an eye.

BACKGROUND

In order to measure refractive correction amounts necessary to prescribe eyeglasses or contact lenses, eye refraction tests are generally conducted.

The eye refraction tests include a subjective refraction test in which a subject responds to shown optotypes or light by oneself, and an objective refraction test in which emitted light is observed from outside of an eyeball.

The subjective refraction test typically employs a lens exchange method. The lens exchange method involves determining the largest refractive power (diopter) that provides the best vision, by exchanging correction lenses with the use of an eyesight test chart. The lens exchange method can be implemented by using only a trial frame for holding a correction lens and an optical trial lens set, but needs repeating the same operation for the eyesight test while slightly changing the refractive power (diopter) of the correction lens, which results in a complicated process. Meanwhile, as to astigmatism correction, it is necessary to compare the current view with the view seen in the immediately prior state that is memorized, by exchanging the correction lenses, and therefore, the process requires labor and patience.

On the other hand, the objective refraction test usually employs a method using an automatic refractometer or a retinoscopy.

Examples of the automatic refractometer include a coincidence refractometer and an image analysis refractometer. The coincidence refractometer emits two (or a plurality of) thin light fluxes to an eyeground and determines a refractive power (diopter) from relative positional relationships between these light fluxes on the eyeground, based on the principle of Scheiner. The image analysis refractometer captures an image that is projected on an eyeground by using an imaging sensor and analyzes the captured image to determine a refractive power (diopter). These automatic refractometers enable a short-time examination that requires no skill of a measurer, but are very expensive.

For example, a method and an apparatus for easily measuring a refractive power (diopter) of an eye by a subjective refraction test have been developed (Patent literature 1).

In these method and apparatus, two separated light beams are alternately emitted from a light source to an eye, and a subject sees light that has passed through one pinhole. At this time, while a rotation plate having the one pinhole is rotated, the two light beams are alternately emitted in synchronization with the pinhole coming to one of two positions opposite to each other by 180 degrees (for example, at the highest position and the lowest position on a vertical straight line). The distance between the light beams is adjusted so that the two light beams will reach the same positions on a retina. The distance between the light beams is measured in the state in which spots of the two light beams come to the same positions on the retina, whereby a refractive power of the eye is calculated. In addition, the two light beams are alternately emitted by using two pinholes, and one of the pinholes is shuttered in synchronization with emission of one of the light beams.

CITATION LIST

Patent Literature

Patent literature 1: U.S. Pat. No. 5,988,814

BRIEF SUMMARY

Technical Problem

However, the above-described apparatus needs devices such as a dedicated device for rotating the rotation plate having the one pinhole at a constant speed, and a dedicated device for emitting a light beam in synchronization with the pinhole coming to one of the predetermined two positions opposite to each other.

In addition, in the case in which the two light beams are alternately emitted by using the two pinholes, a dedicated device for shuttering one of the pinholes in synchronization with emission of one of the light beams.

Thus, the above-described apparatus has a complicated configuration and is not simply structured for a person who measures a refractive power of the eye in subjective refraction test by oneself.

Moreover, this apparatus emits two light beams alternately, and therefore, it is necessary to correctly memorize the previous position on the retina where the light beam reached, in order to determine whether the positions on the retina of the eye where the light beams reached coincide with each other. The refraction power is measured based on the determination for coincidence that depends on the memory, which causes difficulty in obtaining a highly accurate measurement result.

On the other hand, in order to dispense with memorizing the position on the retina where the light beam reached, it is preferable that two light beams are simultaneously emitted and are made to reach an eye by using two pinholes. In this case, however, the two light beams pass through one pinhole, and consequently, there are four positions on the retina of the eye where the light beams reach from the two pinholes. That is, the subject sees four spots of light.

For this reason, in the subjective refraction test in which a subject measures refractive properties of the eye by oneself, it is difficult for the subject to know which of the four reached positions should be compared to each other for position coincidence.

In view of this, an object of the present invention is to provide a refractive property measurement apparatus, a measurement tool, and a refractive property measurement method that enable measuring refractive properties of an eye with high accuracy by using a simple configuration, without requiring a measurer (subject) to memorize a reached position of a light beam.

Solution to Problem

An embodiment of the present disclosure is a refractive property measurement apparatus configured to measure refractive properties of an eye. The refractive property measurement apparatus includes:

a disk provided with a first aperture and a second aperture, the first aperture and the second aperture having a pinhole shape or a slit shape and being configured to transmit incident light rays while narrowing them;

a light emitting unit configured to emit a first light ray and a second light ray from different positions that are equally separated from the disk, on a plane parallel to a surface of the disk, so that the light rays having passed through the first aperture and the second aperture enter the eye simultaneously; and a processing unit configured to determine refractive properties of the eye from information of positions on a retina of the eye where the first light ray having passed through the first aperture and the second light ray having passed through the second aperture reach.

The first aperture including a first optical element that has transmission characteristics of transmitting the first light ray but preventing the second light ray from passing therethough, and the second aperture including a second optical element that has transmission characteristics of transmitting the second light ray but preventing the first light ray from passing therethough.

Preferably, the light emitting unit may be configured such that at least one of the positions for emitting the first light ray and the second light ray is movable therebetween so that the positions for emitting the first light ray and the second light ray are able to be relatively displaced along an aperture arrangement direction of the first aperture and the second aperture.

Preferably, the processing unit may be configured to calculate a refractive power of the eye by using a displacement amount between the positions for emitting the first light ray and the second light ray in a state in which positions in the aperture arrangement direction on the retina of the eye where the first light ray and the second light ray reach, coincide with each other.

Preferably, the apparatus may further include a distance sensor that is configured to measure a distance between a surface for emitting the first light ray and the second light ray of the light emitting unit and the disk, and the processing unit may be configured to calculate the refractive power of the eye from the distance measured by the distance sensor, the displacement amount, and a distance between centers of the first aperture and the second aperture.

Preferably, the first light ray and the second light ray may have different wavelength bands, the first optical element is an optical filter in which a wavelength band may be set so that the first light ray is transmitted but the second light ray is prevented from passing therethough, and the second optical element is an optical filter in which a wavelength band may be set so that the second light ray is transmitted but the first light ray is prevented from passing therethough.

Preferably, the first light ray and the second light ray may be linearly polarized light rays having different polarizing characteristics, the first optical element may be a polarizing plate that is disposed in a direction of transmitting the first light ray but preventing the second light ray from passing therethough, and the second optical element may be a polarizing plate that is disposed in a direction of transmitting the second light ray but preventing the first light ray from passing therethough.

Preferably, the apparatus may further include a support for supporting the disk in such a manner that the aperture arrangement direction of the first aperture and the second aperture is rotatable.

Preferably, the support may be an eyeglasses frame, and the disk is mounted to a lens holder of the eyeglasses frame.

Another embodiment of the present invention is a measurement tool configured to be disposed between positions for emitting a first light ray and a second light ray, and an eye, in measuring refractive properties of the eye that receives the first light ray and the second light ray from forward. The measurement tool includes:

a disk provided with a first aperture and a second aperture, the first aperture and the second aperture having a pinhole shape or a slit shape and being configured to transmit the first light ray and the second light ray entering thereto while narrowing them and to make the transmitted first light ray and second light ray reach a retina of the eye; and a support that fixes the disk in front of the eye.

In order to enable distinguishing between positions on the retina of the eye where the first light ray having passed through the first aperture and the second light ray having passed through the second aperture reach, the first aperture including a first optical element that has transmission characteristics of transmitting the first light ray but preventing the second light ray from passing therethough, and the second aperture including a second optical element that has transmission characteristics of transmitting the second light ray but preventing the first light ray from passing therethough.

Yet another embodiment of the present invention is a refractive property measurement method for measuring refractive properties of an eye. The method includes:

emitting a first light ray and a second light ray from different positions that are equally separated from a disk, on a plane parallel to a surface of the disk, so that incident light rays entering the disk enter the eye simultaneously by passing through a first aperture and a second aperture provided to the disk, the first aperture and the second aperture having a pinhole shape or a slit shape and being configured to transmit the incident light rays while narrowing them; and determining the refractive properties of the eye from information of positions on a retina of the eye where the first light ray having passed through the first aperture and the second light ray having passed through the second aperture reach.

The first aperture including a first optical element that has transmission characteristics of transmitting the first light ray but preventing the second light ray from passing therethough, and the second aperture including a second optical element that has transmission characteristics of transmitting the second light ray but preventing the first light ray from passing therethough.

Preferably, the refractive property measurement method may further include:

relatively displacing the positions for emitting the first light ray and the second light ray, therebetween, along an aperture arrangement direction of the first aperture and the second aperture, so that positions in the aperture arrangement direction on the retina of the eye where the first light ray having passed through the first aperture and the second light ray having passed through the second aperture reach, coincide with each other; and calculating a refractive power of the eye by using an amount of the displacement along the aperture arrangement direction between the positions for emitting the first light ray and the second light ray in the state in which the positions in the aperture arrangement direction on the retina of the eye where the first light ray and the second light ray reach, coincide with each other.

Advantageous Effects

The refractive property measurement apparatus, the measurement tool, and the refractive property measurement method enable highly accurate measurement using a simple configuration, without requiring a measurer (subject) to memorize a reached position of a light beam.

DETAILED DESCRIPTION

Hereinafter, a refractive property measurement apparatus, a measurement tool, and a refractive property measurement method according to an embodiment of the present disclosure will be described based on the attached drawings.
Measurement of Refractive Properties in Embodiment In general, light rays having passed through different two apertures are refracted by a lens and converge into one light ray at a focal point position and diverge into two light rays at a position separated from the focal point position. This principle is known as the principle of Scheiner. In accordance with this principle, when an optotype is shown to a subject of optometry, it is possible to determine whether images of light rays, which are emitted from the optotype and then pass through two pinhole-shaped or slit-shaped apertures, are seen as one image or two images of the optotype through the lens of the eye. However, it is difficult to quantitatively provide a deviation amount between the two images in a subjective manner, for example, a deviation amount in terms of millimeters. However, appropriately displacing one part relative to other part of the optotype allows images of the optotype, which pass through the mutually separated two apertures, to be seen as one image. The displacement amount of the optotype at this time is measured, and the refractive properties of the eye can be determined by using this displacement amount.

In this specification, the refractive properties of an eye include, in addition to refractive properties of a naked eye, refractive properties of an eye that is corrected by a correction lens, that is, combined refractive properties of a naked eye and a correction lens (eyeglasses lens or contact lens). The refractive properties include, in addition to a refractive power, the degree of a refractive power relative to an appropriate refractive power of an eye (described later) (in the case of a naked eye, the type of myopia or hyperopia), and moreover, orientation direction dependence of refractive power and information of a difference between a maximum refractive power and a minimum refractive power, such as in the case of astigmatism.

FIGS. 1A to 1E illustrate measurement of refractive properties in the embodiment. A disk is opened to have pinhole apertures or slit apertures. The following describes an example of pinhole apertures. In the case of using two slit apertures, the two slits are provided in parallel to each other.

Figure 1A:
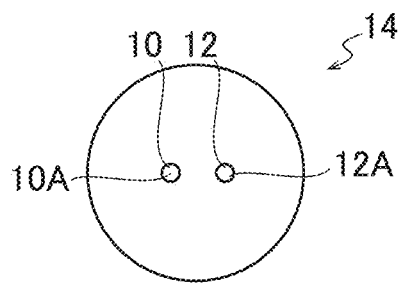
FIGS. 1A to 1E illustrate measurement of refractive properties in an embodiment.

FIG. 1A shows an example of a disk 14 provided with a first pinhole 10 and a second pinhole 12 that transmit incident light rays while narrowing them. The dimensions of the first pinhole 10 and the second pinhole 12 are same. The dimensions (for example, diameter) of the first pinhole 10 and the second pinhole 12 and a distance between centers of the first pinhole 10 and the second pinhole 12 are set to such a degree that the principle of Scheiner will be exhibited. In one example, the first pinhole 10 and the second pinhole 12 have a dimension of 0.5 to 2 mm, and the distance (space) between the centers of the first pinhole 10 and the second pinhole 12 is 2 to 5 mm.

Figure 1B:
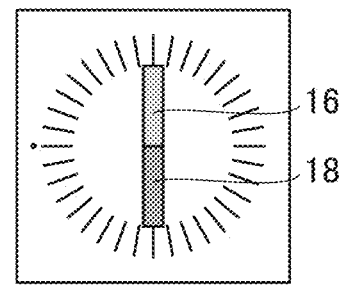

FIG. 1B shows a displayed example of an optotype shown by a light emitting device (light emitting unit) that emits a first light ray L1 and a second light ray L2 so that light rays passing through the first pinhole 10 and the second pinhole 12 will enter one eye simultaneously. The light emitting device is a light source for emitting the first light ray L1 and the second light ray L2 or may be a display for emitting the first light ray L1 and the second light ray L2. FIG. 1B shows an optotype including two rectangular light emitting parts 16 and 18. The light emitting parts 16 and 18 mutually overlap at one side, but they may not overlap each other. Nevertheless, in order to accurately determine whether images of the light emitting parts 16 and 18 on a retina deviate from each other, one sides of the light emitting parts 16 and 18 preferably overlap each other. The light emitting parts 16 and 18 are shown with an angle scale that indicates orientation direction at intervals of 10 degrees. As described later, in order to measure orientation direction dependence of the refractive properties, the light emitting parts 16 and 18 are adjustable in a tilt direction, for example, at intervals of 10 degrees. The scale is used as an indicator when the tilt direction of the light emitting part 16 or 18 is changed.

Note that the following description uses the light emitting parts 16 and 18 that emit light rays by themselves, as an optotype, but the optotype may be printing that emits the first light ray L1 and the second light ray L2 by reflecting incident light rays. That is, the light emitting unit, which includes the light emitting device as an example, also includes printing that emits the first light ray L1 and the second light ray L2 by reflecting light rays.

Figure 1C:
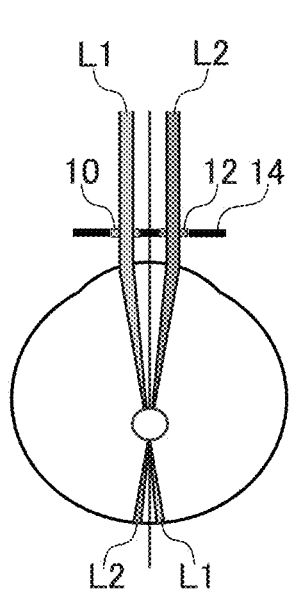
Figure 1D:
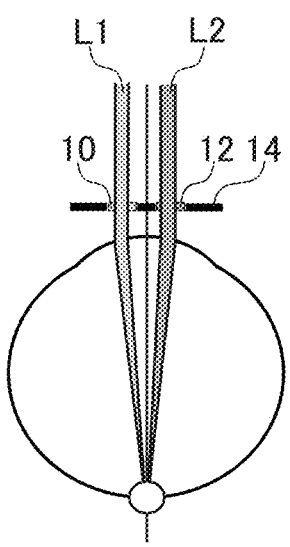
Figure 1E:
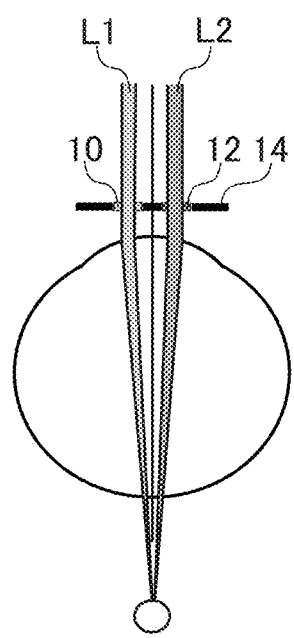

FIGS. 1C to 1E show examples of light paths when the first light ray L1 and the second light ray L2 emitted from the light emitting parts 16 and 18 enter the first pinhole 10 and the second pinhole 12. As shown in FIG. 1D, in the case in which the refractive properties of an eye are appropriate, the position on the retina where the first light ray L1 having passed through the first pinhole 10 reaches, and the position on the retina where the second light ray L2 having passed through the second pinhole 12 reaches, coincide with each other in the aperture arrangement direction of the first pinhole 10 and the second pinhole 12. That is, a measurer (subject) sees images of the first light ray L1 and the second light ray L2 overlapping in the aperture arrangement direction. Thus, in the case in which the images of the first light ray L1 and the second light ray L2 that overlap each other are viewed, the refractive properties of the eye are appropriate or have an appropriate refractive power.

On the other hand, as shown in FIG. 1C, the first light ray L1 and the second light ray L2 cross each other before reaching the retina to cause deviation therebetween in the following case: the refractive power of the eye is greater than an appropriate refractive power of the eye, for example, the eye has myopia or the refractive power of a corrected eye (the total of the refractive powers of the eye and a correction lens) is greater than an appropriate refractive power of the eye. In the example shown in FIG. 1C, the first light ray L1 deviates to the right in the aperture arrangement direction of the second light ray L2. The aperture arrangement direction represents the arrangement direction of the first pinhole 10 and the second pinhole 12. The aperture arrangement direction shown in FIG. 1A is a horizontal direction.

In contrast, as shown in FIG. 1E, the first light ray L1 and the second light ray L2 do not cross each other on the retina and reach the retina before crossing each other, in the following case: the refractive power of the eye is smaller than an appropriate refractive power of the eye, for example, the eye has hyperopia or the refractive power of a corrected eye (the total of the refractive powers of the eye and a correction lens) is smaller than an appropriate refractive power of the eye. This causes the first light ray L1 and the second light ray L2 to deviate from each other on the retina. In the example shown in FIG. 1E, the first light ray L1 deviates to the left in the aperture arrangement direction of the second light ray L2.

From these points of view, in this embodiment, in the case in which the refractive power of an eye is not appropriate, the light emitting parts 16 and 18 are mutually displaced along the arrangement direction in advance so that the positions on the retina where the first light ray L1 and the second light ray L2 reach, will coincide with each other in the aperture arrangement direction.

Figure 2A:
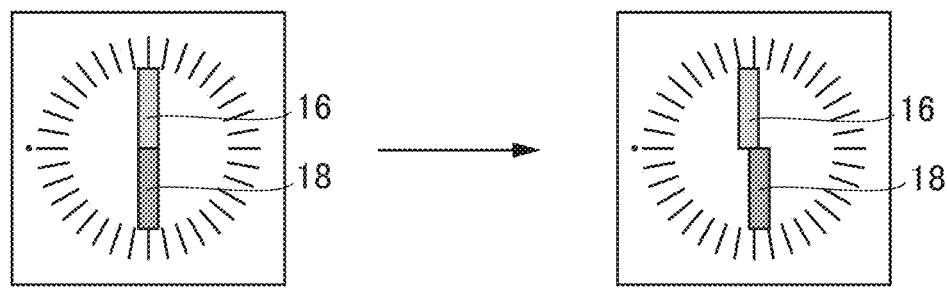
FIGS. 2A and 2B show examples of actual light emitting parts and images of the light emitting parts seen by an eye in measuring refractive properties in the embodiment.
Figure 2B:
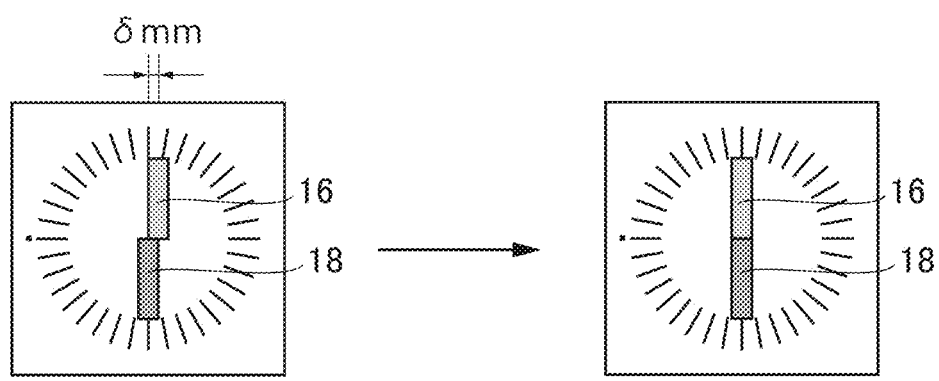

FIGS. 2A and 2B show examples of actual light emitting parts 16 and 18 and images of the light emitting parts 16 and 18 seen by an eye. The example in FIG. 2A shows an image seen in the condition in FIG. 1C. As shown on the left in FIG. 2A, the actual light emitting parts 16 and 18 are not displaced from each other. In this case, as shown on the right in FIG. 2A, the measurer (subject) sees the images of the light emitting parts 16 and 18 deviating from each other in such a manner that the image of the light emitting part 16 deviates to the left of the image of the light emitting part 18 in the horizontal direction (aperture arrangement direction). The deviation is seen as deviation in a direction opposite to the direction of deviation on the retina due to effects of the optic nerve.

Conversely, as shown on the left in FIG. 2B, the actual light emitting parts 16 and 18 are relatively displaced. For example, assuming that the light emitting part 16 is displaced in the aperture arrangement direction relative to the light emitting part 18 by an appropriate displacement amount $\delta$, the measurer (subject) sees the images of the light emitting parts 16 and 18 coinciding with each other in the horizontal direction (aperture arrangement direction), as shown on the right in FIG. 2B. Note that the light emitting parts 16 and 18 may be relatively displaced in such a manner that one of the light emitting parts 16 and 18 is relatively displaced or both of the light emitting parts 16 and 18 are relatively displaced in mutually opposite directions of the aperture arrangement direction.

Thus, the refractive power of an eye is determined in accordance with the formula (2) described later, by measuring the displacement amount $\delta$ shown in FIG. 2B.

With such a principle, the refractive properties of an eye are measured in this embodiment.

However, the first light ray L1, which is emitted from the light emitting part 16, passes through the second pinhole 12 in addition to the first pinhole 10. In this case, there are two reached positions on a retina of the first light ray L1. Similarly, the second light ray L2, which is emitted at the same time as the first light ray L1, passes through the first pinhole 10 in addition to the second pinhole 12, whereby there are two reached positions on a retina of the second light ray L2. As a result, a measurer (subject) who does not have an appropriate refractive power of the eye sees four images of the light emitting parts 16 and 18. This makes it difficult to correctly determine existence of deviation between the images of the light emitting parts 16 and 18.

In one embodiment, as shown in FIG. 1A, the first pinhole 10 includes a first optical element 10A, and the second pinhole 12 includes a second optical element 12A. The first optical element 10A has transmission characteristics of transmitting the first light ray L1 but preventing the second light ray L2 from passing therethrough. The second optical element 12A has transmission characteristics of transmitting the second light ray L2 but preventing the first light ray L1 from passing therethrough.

With this structure, the light ray that reaches the retina by passing through the first pinhole 10 is the first light ray L1, and the light ray that reaches the retina by passing through the second pinhole 12 is the second light ray L2. Thus, the first light ray L1 does not reach the retina by passing through the second pinhole 12, and the second light ray L2 does not reach the retina by passing through the first pinhole 10. As a result, the measurer (subject) sees one image of each of the light emitting parts 16 and 18, whereby existence of deviation between the light emitting parts 16 and 18 is correctly determined.

Refractive Property Measurement Apparatus

Figure 3:
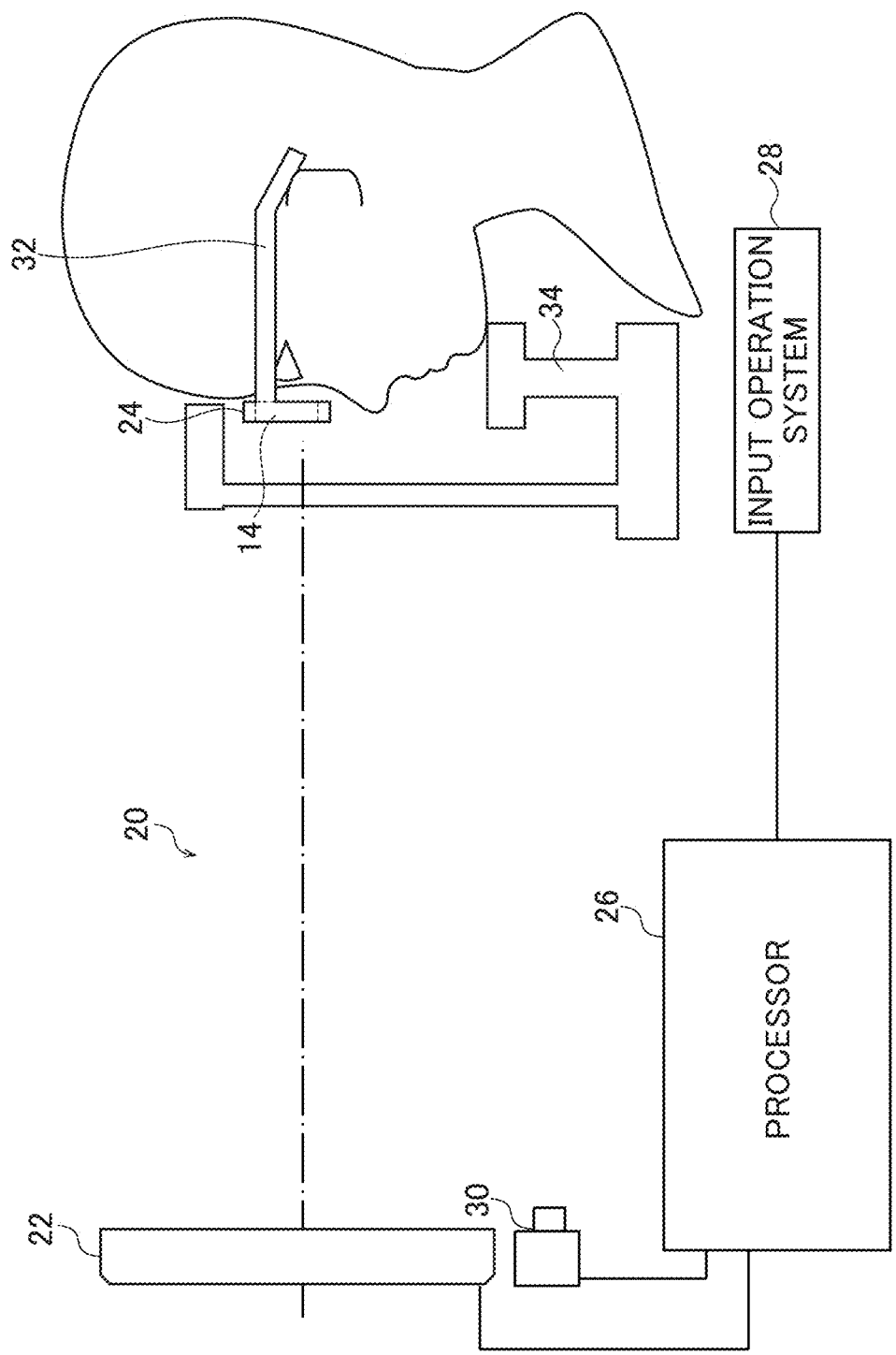
FIG. 3 illustrates a configuration of a refractive property measurement apparatus of the embodiment.

FIG. 3 illustrates a configuration of a refractive property measurement apparatus 20 of an embodiment.

The refractive property measurement apparatus 20 mainly includes a disk 14, a light emitting device (light emitting unit) 22, and a processor (processing unit) 26.

The disk 14 is provided with a first pinhole 10 and a second pinhole 12 that transmit incident light rays while narrowing them, as described above. The disk 14 is put on a measurer (subject) in the form of measurement eyeglasses 32 in which the disk 14 is supported by an eyeglass frame 24.

The light emitting device 22 emits the first light ray L1 and the second light ray L2 so that light rays passing through the first pinhole 10 and the second pinhole 12 will enter the eye simultaneously. The emission positions of the first light ray L1 and the second light ray L2 of the light emitting device 22 are equally separated from the disk 14 and are different from each other on a plane parallel to the surface of the disk 14. The light emitting device 22 is provided on a side opposite to the eye across the disk 14. The light emitting device 22 shown in FIG. 3 is a display connected to the processor 26. Note that the light emitting device 22 is not limited to a display and may be made of two light sources.

The processor 26 is composed of, for example, a computer, and is configured to determine refractive properties of an eye from information of positions on a retina of the eye where the first light ray L1 having passed through the first pinhole 10 and the second light ray L2 having passed through the second pinhole 12 reach. As described above, the refractive properties of an eye include, in addition to a refractive power, at least information of degree of a refractive power of an eye relative to an appropriate refractive power (in the case of a naked eye, the type of myopia, hyperopia, or the like). The processor 26 is connected to the light emitting device 22 and is also connected to an input operation system 28. The calculation of a refractive power that is performed by the processor 26 will be described later.

The input operation system 28 is composed of, for example, a keyboard and/or a mouse, and by which the measurer (subject) can input instructions so as to change the arrangement direction, displacement, and so on of the light emitting parts 16 and 18 of the light emitting device 22. Thus, the displacement amount between the light emitting parts 16 and 18 of the light emitting device 22 can be input, as an instruction, to the processor 26 via the input operation system 28, so that the images of the light emitting parts 16 and 18 seen by the measurer (subject) will not deviate from each other. The processor 26 controls in response to the input displacement amount, to make the light emitting device 22 display mutually-displaced light emitting parts 16 and 18 as an optotype, as shown in FIG. 2B.

The refractive property measurement apparatus 20 also includes a distance sensor 30 and a base 34 on which the face is placed so that the eye of the measurer (subject) will be disposed at a predetermined position.

The distance sensor 30 measures an observation distance "d" (refer to FIG. 4) from the light emitting device 22 to the disk 14, in order to calculate a correct refractive power in measurement of refractive properties. The distance sensor 30 can employ, for example, a laser rangefinder. The results that are measured by the distance sensor 30 are transmitted to the processor 26.

Figure 4:
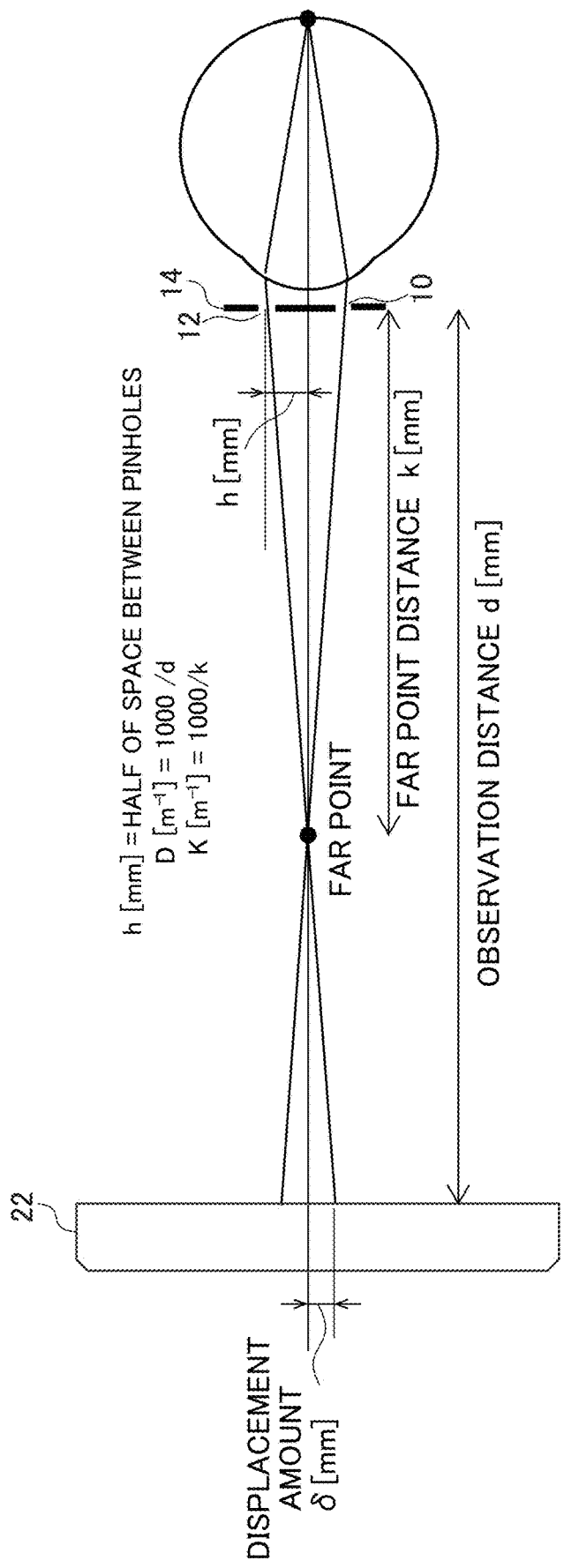
FIG. 4 illustrates a method of calculating a refractive power of an eye, which is performed by a processor of the embodiment.

FIG. 4 illustrates a method of calculating a refractive power of an eye, which is performed by the processor 26. It is assumed that an observation distance between the light emitting device 22 and the disk 14 is represented as "d [mm]", a far point distance is represented as "k [mm]", a displacement amount between the light emitting parts 16 and 18 that is adjusted so as to eliminate deviation in the aperture arrangement direction between images of the light emitting parts 16 and 18 seen by the measurer (subject) is represented as "δ [mm]", and a half of a distance between centers of the first pinhole 10 and the second pinhole 12 is represented as "h [mm]". In these conditions, the displacement amount δ and a refractive power "K" are represented by the following formulas (1) and (2). Thus, the processor 26 calculates the refractive power "K" by using the formula (2). The value "D" is calculated from the observation distance "d", which is obtained in measurement performed by the distance sensor 30. The space between the first pinhole 10 and the second pinhole 12 is known, and thus, the value "h" is also known. The value "δ", which is set through the input operation system 28, is also known by the processor 26. The far point distance "k" is determined as an inverse of the refractive power "K".

$$\delta = h \cdot (D-K)/D \quad (1)$$

$$K = D \cdot (h-\delta)/h \quad (2)$$

$$(D[m^{-1}]=1000/d, K[m^{-1}]=1000/k)$$

Note that the displacement amount δ is positive in the upper direction and is negative in the lower direction on the paper surface of FIG. 4. FIG. 4 shows an example of a negative displacement amount δ.

In this embodiment, the first pinhole 10 includes the first optical element 10A, and the second pinhole 12 includes the second optical element 12A. The first optical element 10A has transmission characteristics of transmitting the first light ray L1 but preventing the second light ray L2 from passing therethrough. The second optical element 12A has transmission characteristics of transmitting the second light ray L2 but preventing the first light ray L1 from passing therethrough. Thus, the number of the images of the light emitting parts 16 and 18 that are projected on the retina at the same time is two. With this structure, existence of deviation between the light emitting parts 16 and 18 is correctly determined, and it is not necessary for the measurer (subject) to memorize one of the positions of the light emitting parts 16 and 18, whereby the measurement is performed with high accuracy. Moreover, unlike conventional apparatuses, there is no need to use a dedicated device for emitting light rays, like strobe light, in synchronization with a rotation position of a pinhole that is rotated. Thus, refractive properties of an eye can be measured by the simple configuration.

In one embodiment, the first light ray L1 and the second light ray L2 are preferably linearly polarized light rays having different polarizing characteristics. In addition, the first optical element 10A is preferably a polarizing plate that is disposed so as to transmit the first light ray L1 but prevent the second light ray L2 from passing therethrough, and the second optical element 12A is preferably a polarizing plate that is disposed so as to transmit the second light ray L2 but prevent the first light ray L1 from passing therethrough. In these conditions, the light ray that enters an eye from the first pinhole 10 is the first light ray L1, and the light ray that enters an eye from the second pinhole 12 is the second light ray L2.

In one embodiment, the first light ray L1 and the second light ray L2 are preferably light rays having different wavelength bands (that is, the first light ray L1 and the second light ray L2 preferably have different colors). In addition, the first optical element 10A is preferably an optical filter in which the wavelength band is set so that the first light ray L1 will be transmitted but the second light ray L2 will be prevented from passing therethrough, and the second optical element 12A is preferably an optical filter in which the wavelength band is set so that the second light ray L2 will be transmitted but the first light ray L1 will be prevented from passing therethrough. In these conditions, the light ray that enters an eye from the first pinhole 10 is the first light ray L1, and the light ray that enters an eye from the second pinhole 12 is the second light ray L2. Moreover, the measurer (subject) can easily distinguish which colored light ray deviates to the right of the other light ray, from the color of the light of the light emitting part 16 or 18 that occurs deviation. Thus, it is easy to determine the degree of the refractive power of the eye relative to an appropriate refractive power of the eye (in the case of a naked eye, the type of myopia or hyperopia).

As described above, the light emitting device 22 is configured such that at least one of the positions for emitting the first light ray L1 and the second light ray L2 is movable therebetween so that they are relatively displaced along the aperture arrangement direction. This structure enables eliminating deviation in the aperture arrangement direction between the images of the light emitting parts 16 and 18 seen by the measurer (subject), by adjusting a displacement amount between the actual light emitting parts 16 and 18 of the light emitting device 22, as shown in FIG. 2B. Thus, a refractive power is calculated with high accuracy.

The processor 26 is configured to calculate a refractive power of an eye by using a displacement amount along the aperture arrangement direction between the positions for emitting the first light ray L1 and the second light ray L2 in the state in which positions in the aperture arrangement direction on the retina where the first light ray L1 emitted from the light emitting part 16 and the second light ray L2 emitted from the light emitting part 18 reach, coincide with each other. Thus, a refractive power is calculated with high accuracy by the simple formula, as shown by the formula (2).

The refractive property measurement apparatus 20 includes the distance sensor 30 that measures the distance between the surface for emitting the first light ray L1 and the second light ray L2 of the light emitting device 26 and the disk 14. This structure enables calculating a refractive power with high accuracy by using the formula (2), although the base 34 is freely located relative to the light emission surface 22.

Figure 5A:
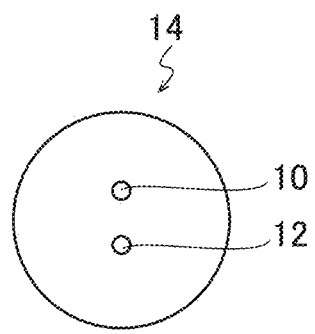
FIGS. 5A to 5D illustrate other examples of measurement of refractive properties of an eye.
Figure 5B:
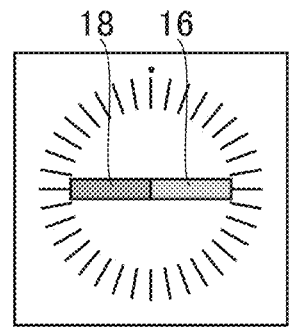

FIGS. 5A to 5D illustrate other examples of measurement of refractive properties of an eye. In the above-described embodiment, as shown in FIG. 1A, the aperture arrangement direction, which is the arrangement direction of the first pinhole 10 and the second pinhole 12, is in the horizontal direction, and therefore, refractive properties in the horizontal direction of an eye are measured. In the case of measuring refractive properties in the vertical direction of an eye, the aperture arrangement direction is set in the vertical direction, as shown in FIG. 5A. In addition, as shown in FIG. 5B, the directions of the light emitting parts 16 and 18 as the optotype are changed so that the arrangement direction thereof also will be the horizontal direction. In these conditions, the displacement amount δ between the light emitting parts 16 and 18 is determined so that the images of the light emitting parts 16 and 18 seen by the measurer (subject) will not deviate from each other but coincide with each other in the aperture arrangement direction. As a result, refractive properties in the vertical direction of the eye are measured, and the processor 26 can calculate a refractive power in the vertical direction of the eye in accordance with the formula (2).

Figure 5C:
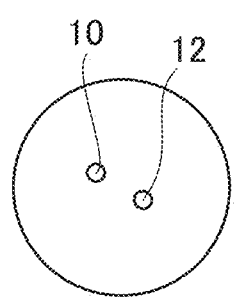
Figure 5D:
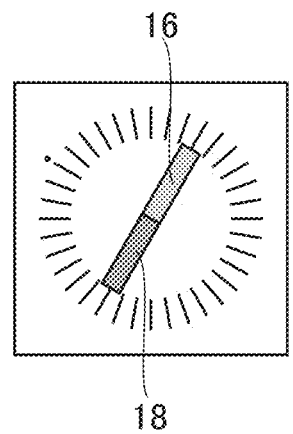

FIGS. 5C and 5D show an example of a case of measuring refractive properties of an eye in a direction tilted relative to the horizontal direction by 30 degrees. In the example shown in FIGS. 5C and 5D, the aperture arrangement direction is an orientation direction tilted relative to the horizontal direction by 30 degrees. In addition, as shown in FIG. 5D, the directions of the light emitting parts 16 and 18 as the optotype are changed so that they also will face a direction tilted relative to the vertical direction by 30 degrees. In these conditions, the displacement amount δ along the aperture arrangement direction between the light emitting parts 16 and 18 is set so that the positions of the images of the light emitting parts 16 and 18 seen by the measurer (subject) will not deviate from each other but coincide with each other in the aperture arrangement direction. As a result, refractive properties of an eye in the orientation direction tilted relative to the horizontal direction by 30 degrees are measured, and the processor 26 can calculate a refractive power of the eye in the direction (hereinafter, this direction is called an "orientation direction") tilted relative to the horizontal direction by 30 degrees, in accordance with the formula (2).

Figure 6:
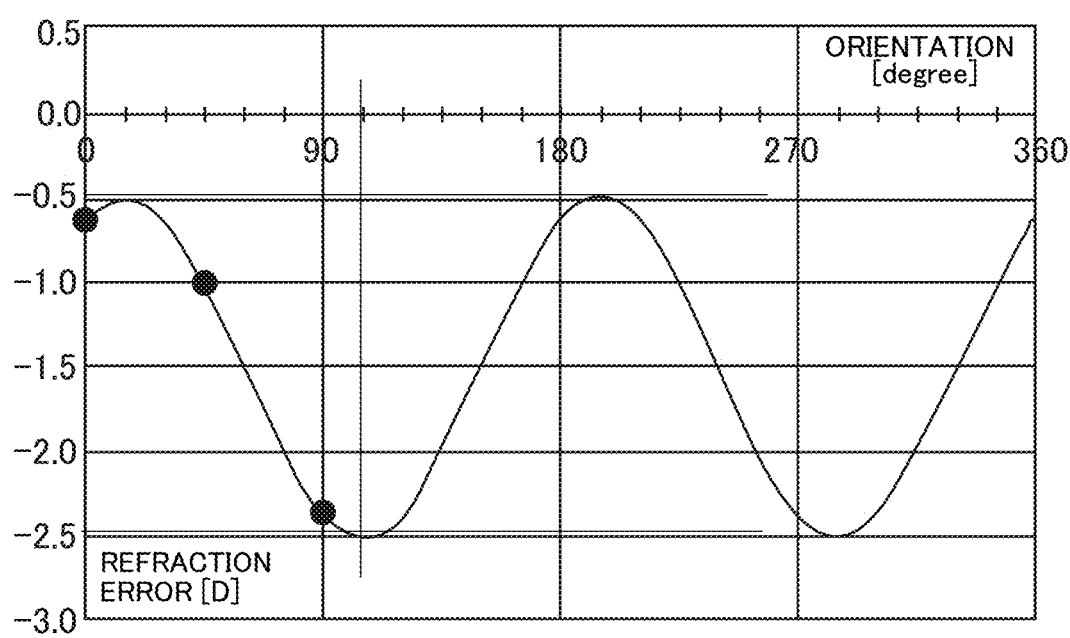
FIG. 6 shows an example of direction dependence of refractive power of an eye.

In one example, measurement and calculation of at least three orientation directions, such as a horizontal direction, a vertical direction, and an orientation direction of 45 degrees of an eye, provide information of variations in the orientation direction of a refractive power of the eye. FIG. 6 shows an example of orientation direction dependence of refractive power of an eye (described as "refraction error" in the drawing). In the example in FIG. 6, after refractive powers in a horizontal direction (orientation of 0 degrees), a vertical direction (orientation of 90 degrees), and a tilt direction (orientation of 45 degrees) are measured, a sine wave curve is fitted to the results. This provides information of orientation direction dependence of the refractive power of the eye. From this information, the orientation directions at which the refractive powers of the eye are maximum and minimum are known, and, for example, information of direction of an astigmatism axis and strength of astigmatism (difference between the maximum refractive power and the minimum refractive power) is obtained. Such processing is performed by the processor 26, and information of orientation direction dependence of refractive power of an eye is obtained as refractive properties.

In consideration of this, the support 24 (refer to FIG. 3) for supporting the disk 14 preferably supports the disk 14 in such a manner that the aperture arrangement direction, which is the arrangement direction of the first pinhole 10 and the second pinhole 12, is rotatable. This facilitates measurement of orientation direction dependence of refractive properties of an eye.

The support 24 is, for example, an eyeglasses frame, and the disk 14 is preferably mounted to a lens holder of the eyeglasses frame. This structure enables reliably disposing the disk 14 in front of an eye.

The refractive property measurement apparatus 20 described above facilitates measurement of refractive properties of an eye. Another embodiment provides a measurement tool to be disposed between the emission positions of the first light ray L1 and the second light ray L2 and an eye in measuring refractive properties of the eye that receives the first light ray L1 and the second light ray L2 from forward. An example of the measurement tool includes the eyeglasses frame described above.

In this case, the measurement tool includes a disk and a support.

As in the case of the disk 14, this disk is provided with a first pinhole 10 and a second pinhole 12 that is configured to transmit incident first light ray L1 and second light ray L2 while narrowing them and to make the transmitted first light ray L1 and second light ray L2 reach a retina of an eye.

Also in this disk, in order to distinguish between the positions on a retina of an eye where the first light ray L1 having passed through the first pinhole 10 and the second light ray L2 having passed through the second pinhole 12 reach, the first pinhole 10 includes a first optical element 10A, and the second pinhole 12 includes a second optical element 12A. The first optical element 10A has transmission characteristics of transmitting the first light ray L1 but preventing the second light ray L2 from passing therethrough. The second optical element 12A has transmission characteristics of transmitting the second light ray L2 but preventing the first light ray L1 from passing therethrough.

With the use of such a measurement tool, the measurer (subject) can measure refractive properties of the eye. In this case, prepared light emitting parts 16 and 18 are used. For example, the light emitting parts 16 and 18 that are drawn on a display, which is connected to a computer, can be used as an optotype. Of course, printing can also be used as an optotype that uses reflection light.

One embodiment provides a refractive property measurement method including:

(1) emitting a first light ray L1 and a second light ray L2 from different positions that are equally separated from a disk 14 in a depth direction seen from a side of an eye to be measured, on a plane parallel to a surface of the disk 14, so that incident light rays entering the disk 14 will enter the eye simultaneously by passing through a first pinhole 10 and a second pinhole 12, which are provided to the disk 14 so as to transmit the incident light rays while narrowing them; and (2) determining refractive properties of the eye from information of positions in an aperture arrangement direction on the retina of the eye where the first light ray L1 having passed through the first pinhole 10 and the second light ray L2 having passed through the second pinhole 12 reach.

(3) In this case, the first pinhole 10 includes a first optical element 10A, and the second pinhole 12 includes a second optical element 12A. The first optical element 10A has transmission characteristics of transmitting the first light ray L1 but preventing the second light ray L2 from passing therethrough. The second optical element 12A has transmission characteristics of transmitting the second light ray L2 but preventing the first light ray L1 from passing therethrough.

In these conditions, in one embodiment, (4) the positions for emitting the first light ray L1 and the second light ray L2 are relatively displaced therebetween along the aperture arrangement direction of the first pinhole 10 and the second pinhole 12 so that positions in the aperture arrangement direction on the retina of the eye where the first light ray L1 having passed through the first pinhole 10 and the second light ray L2 having passed through the second pinhole 12 reach, will coincide with each other; and (5) a refractive power of the eye is calculated by using a displacement amount δ along the aperture arrangement direction between the positions for emitting the first light ray L1 and the second light ray L2 in the state in which the positions in the aperture arrangement direction on the retina of the eye where the first light ray L1 and the second light ray L2 reach, coincide with each other. This facilitates calculation of the refractive power of the eye.

Although the refractive property measurement apparatus, the measurement tool, and the refractive property measurement method of the present invention are detailed above, the present invention is not limited to the above-described embodiments, and, of course, can be variously modified and altered without departing from the gist of the present invention.

REFERENCE SIGNS LIST 10 first pinhole
10A first optical element
12 second pinhole
12A second optical element
14 disk
16, 18 light emitting part
20 refractive property measurement apparatus
22 light emitting device
24 support
26 processor
28 input operation system
30 distance sensor
32 measurement eyeglasses
34 base

The invention claimed is:

1. A refractive property measurement apparatus configured to measure refractive properties of an eye, the apparatus comprising:

a disk provided with a first aperture and a second aperture, the first aperture and the second aperture having a pinhole shape or a slit shape and being configured to transmit incident light rays while narrowing them;

a light emitting unit configured to emit a first light ray and a second light ray from different positions that are equally separated from the disk, on a plane parallel to a surface of the disk, so that the light rays having respectively passed through the first aperture and the second aperture enter the eye simultaneously; and a processing unit configured to determine refractive properties of the eye from information of positions on a retina of the eye where the first light ray having passed through the first aperture and the second light ray having passed through the second aperture reach, wherein the first aperture including a first optical element that has transmission characteristics of transmitting the first light ray but preventing the second light ray from passing therethrough, the second aperture including a second optical element that has transmission characteristics of transmitting the second light ray but preventing the first light ray from passing therethrough, the first light ray and the second light ray have different wavelength bands, the first optical element is an optical filter in which a wavelength band is set so that the first light ray is transmitted but the second light ray is prevented from passing therethrough, the second optical element is an optical filter in which a wavelength band is set so that the second light ray is transmitted but the first light ray is prevented from passing therethrough, and the processing unit is configured to determine the refractive properties of the eye based on positions of images of the first light ray and the second light ray on a retina.

2. The refractive property measurement apparatus according to claim 1, wherein the light emitting unit is configured such that at least one of the positions for emitting the first light ray and the second light ray is movable therebetween so that the positions for emitting the first light ray and the second light ray are able to be relatively displaced along an aperture arrangement direction of the first aperture and the second aperture.

3. The refractive property measurement apparatus according to claim 2, wherein the processing unit is configured to calculate a refractive power of the eye by using a displacement amount between the positions for emitting the first light ray and the second light ray in a state in which positions in the aperture arrangement direction on the retina of the eye where the first light ray and the second light ray reach, coincide with each other.

4. The refractive property measurement apparatus according to claim 3, further comprising:

a distance sensor that is configured to measure a distance between a surface for emitting the first light ray and the second light ray of the light emitting unit and the disk, the processing unit being configured to calculate the refractive power of the eye from the distance measured by the distance sensor, the displacement amount, and a distance between centers of the first aperture and the second aperture.

5. The refractive property measurement apparatus according to claim 2, further comprising:
a support for supporting the disk in such a manner that the aperture arrangement direction of the first aperture and the second aperture is rotatable.

6. The refractive property measurement apparatus according claim 1, further comprising:
a support for supporting the disk in such a manner that the aperture arrangement direction of the first aperture and the second aperture is rotatable.

7. The refractive property measurement apparatus according to claim 6, wherein the support is an eyeglasses frame, and the disk is mounted to a lens holder of the eyeglasses frame.

8. A measurement tool configured to be disposed between positions for emitting a first light ray and a second light ray, and an eye, in measuring refractive properties of the eye that receives the first light ray and the second light ray from forward, the tool comprising:
a disk provided with a first aperture and a second aperture, the first aperture and the second aperture having a pinhole shape or a slit shape and being configured to transmit the first light ray and the second light ray entering respective first aperture and second aperture simultaneously while narrowing the first light ray and the second light ray respectively, and to make the transmitted first light ray and second light ray reach a retina of the eye simultaneously; and
a support that fixes the disk in front of the eye, wherein in order to enable distinguishing between positions on the retina of the eye where the first light ray having passed through the first aperture and the second light ray having passed through the second aperture reach,
the first aperture including a first optical element that has transmission characteristics of transmitting a wavelength band so that the first light ray can pass through but preventing the second light ray from passing therethrough, and
the second aperture including a second optical element that has transmission characteristics of transmitting a wavelength band so that the second light ray can pass through but preventing the first light ray from passing therethrough.

9. A refractive property measurement method for measuring refractive properties of an eye, the method comprising:
emitting a first light ray and a second light ray from different positions that are equally separated from a disk, on a plane parallel to a surface of the disk, so that incident light rays entering the disk enter the eye simultaneously by passing respectively through a first aperture and a second aperture provided to the disk, the first aperture and the second aperture having a pinhole shape or a slit shape and being configured to transmit the respective incident light rays simultaneously while narrowing them; and
determining the refractive properties of the eye from information of positions on a retina of the eye where the first light ray having passed through the first aperture and the second light ray having passed through the second aperture reach,
wherein the first aperture including a first optical element that has transmission characteristics of transmitting a wavelength band so that the first light ray can pass through but preventing the second light ray from passing therethrough,
the second aperture including a second optical element that has transmission characteristics of transmitting a wavelength band so that the second light ray can pass through but preventing the first light ray from passing therethrough.

10. The refractive property measurement method according to claim 9, further comprising:
relatively displacing the positions for emitting the first light ray and the second light ray, therebetween, along an aperture arrangement direction of the first aperture and the second aperture, so that positions in the aperture arrangement direction on the retina of the eye where the first light ray having passed through the first aperture and the second light ray having passed through the second aperture reach, coincide with each other; and
calculating a refractive power of the eye by using an amount of the displacement along the aperture arrangement direction between the positions for emitting the first light ray and the second light ray in the state in which the positions in the aperture arrangement direction on the retina of the eye where the first light ray and the second light ray reach, coincide with each other.

\* \* \* \* \*